United States Patent [19]

Campbell et al.

[11] 4,188,391
[45] Feb. 12, 1980

[54] 4-[4-(SUBSTITUTED)PIPERIDINO]-QUINAZOLINE CARDIAC STIMULANTS

[75] Inventors: Simon F. Campbell, Deal; John C. Danilewicz, Ash, Nr. Canterbury; Allan L. Ham, Broadstairs; John K. Stubbs, Deal, all of England

[73] Assignee: Pfizer Inc., New York, N.Y.

[21] Appl. No.: 954,931

[22] Filed: Oct. 26, 1978

[30] Foreign Application Priority Data

Nov. 3, 1977 [GB] United Kingdom ............... 45669/77

[51] Int. Cl.² ................... A61K 31/505; C07D 401/04
[52] U.S. Cl. ..................................... 424/251; 544/293; 546/301
[58] Field of Search ......................... 544/293; 424/251

[56] References Cited

U.S. PATENT DOCUMENTS

| | | | |
|---|---|---|---|
| 3,517,005 | 6/1970 | Cronin et al. | 544/293 |
| 3,594,480 | 7/1971 | Cronin et al. | 424/251 |
| 3,812,127 | 5/1974 | Cronin et al. | 544/293 |
| 4,001,422 | 1/1977 | Danilewiez et al. | 544/293 |

Primary Examiner—Paul M. Coughlan, Jr.
Attorney, Agent, or Firm—Connolly and Hutz

[57] ABSTRACT

6,7-Dialkoxy-4-[4-(substituted)piperidino]quinazolines wherein the 4-substituent is $-(CHR^1)_m-Z$ wherein $R^1$ is hydrogen or lower alkyl; m is 1 or 2, with the proviso that when m is 2, each $R^1$ can be the same or different; Z is $-N(R^2)COR^3$, $-OCONR^4R^5$, $N(R^2)SO_2R^3$ or $-N(R^2)CONR^4R^5$ wherein $R^2$ is hydrogen or lower alkyl; $R^3$ is lower alkyl, benzyl or phenyl; and each of $R^4$ and $R^5$ is hydrogen or is selected from group $R^3$; and methods for their preparation. The compounds are phosphodiesterase inhibitors and cardiac stimulants.

13 Claims, No Drawings

4-[4-(SUBSTITUTED)PIPERIDINO]QUINAZOLINE CARDIAC STIMULANTS

BACKGROUND OF THE INVENTION

1. Field of the Invention

This invention relates to therepeutic agents, which are novel derivatives of quinazoline, and is particularly concerned with such derivatives having a substituted piperidino group in the 4-position. The compounds of the invention are phosphodiesterase inhibitors and cardiac stimulants.

The compounds are useful in the curative or prophylactic treatment of cardiac conditions, particularly heart failure.

2. Description of the Prior Art

Quinazoline compounds, especially those substituted at the 2- and/or the 4-positions with various groups are known to exhibit valuable therapeutic properties. U.S. Pat. Nos. 3,517,005; 3,594,480 and 3,812,127 describe 6,7-dialkoxy-4-[4-(substituted)piperidino]quinazolines wherein the 4-substituent is, for example, alkyl, aryloxycarbonyl, alkoxycarbonyl and substituted alkoxycarbonyl wherein said substituent is formamido, alkylamido, amino, mono- and dialkylamino, which are useful as bronchodilators and as antihypertensive agents.

U.S. Pat. No. 4,001,422 discloses a series of 6,7-dialkoxy-4-substituted quinazolines wherein the 4-substituent is, inter alia

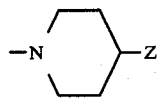

wherein Z is -CH$_2$-COR°; -N(Y$_1$)-COR°; -N(Y$_1$)SO$_2$R°; -N(Y$_1$)-SO$_2$NXY$_2$; -CH$_2$-CONXY$_2$; -OCO-NXY$_2$ and -N(Y$_1$)-CONXY$_2$ wherein R° is lower alkyl or aryl; each of X and Y$_1$ is hydrogen or lower alkyl; and Y$_2$ is hydrogen, lower alkyl or aryl, said compounds being useful as cardiac stimulants.

SUMMARY OF THE INVENTION

According to the invention there is provided novel quinazoline compounds of the formula:

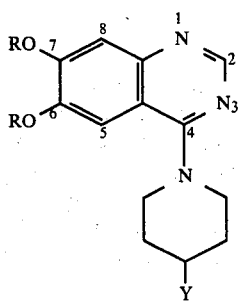

wherein R is a lower alkyl group; and
Y represents a group of the formula:

-(CHR$^1$)$_m$-Z wherein R$^1$ is a hydrogen atom or a lower alkyl group; and m is 1 or 2, with the proviso that when m is 2, each R$^1$ may be the same or different; and Z is a group selected from:
- -OCONR$^4$R$^5$,
- -N(R$^2$)COR$^3$,
- -N(R$^2$)SO$_2$R$^3$, and
- -N(R$^2$)CONR$^4$R$^5$, wherein R$^2$ is hydrogen or lower alkyl, R$^3$ is lower alkyl, benzyl, or phenyl, and R$^4$ and R$^5$ are each independently hydrogen or a group as defined for R$^3$ above; and the pharmaceutically acceptable acid addition salts thereof.

The term "lower" applied to an alkyl or alkoxy group indicates that such a group contains up to 6 carbon atoms, preferably up to 4 carbon atoms, and such groups may be straight or, when appropriate, branched chain.

The compounds of the invention containing one or more asymmetric centers will exist as one or more pairs of enantiomers, and such pairs or individual isomers are separable by physical methods, e.g. by fractional crystallization of suitable salts. The invention includes the separated pairs as well as mixtures thereof, as racemic mixtures or as separated d- and l-optically-active isomeric forms.

The pharmaceutically acceptable acid addition salts of the compounds of the invention are those formed from acids which form non-toxic acid addition salts containing pharmaceutically acceptable anions, such as the hydrochloride, hydrobromide, hydroiodide, sulphate or bisulphate, phosphate or acid phosphate, acetate, maleate, fumarate, lactate, tartrate, citrate, gluconate, saccharate and p-toluenesulphonate salts.

The cardiac stimulant activity of the compounds of the invention is shown by their effectiveness in one or more of the following tests: (a) increasing the force of contraction in the isolated, spontaneously beating, guinea pig double atria preparation; (b) increasing myocardial contractility (left ventricular dP/$_{dt}$ max.) in the anesthetized dog with a left ventricular catheter; (c) increasing myocardial contractility in the conscious dog with an implanted left ventricular transducer.

In test (a) the positive inotropic and chronotropic responses of the atria to the test compound are measured at several doses and compared with the responses elicited by isoprenaline. The comparison of the dose response curves obtained gives a measure of the force versus rate selectivity of the test compound.

In test (b) the positive inotropic action of the test compound following intravenous administration is measured in the anesthetized dog. The magnitude and duration of the inotropic action and the selectivity for increase in force versus frequency of contraction of the test compound are obtained, as are its peripheral effects, e.g. the effect on the blood pressure.

In test (c) the positive inotropic action of the test compound following intravenous or oral administration to a conscious dog with an implanted left ventricular transducer is measured. The magnitude and duration of this action and the selectivity for increase in force versus frequency of contraction of the test compound are all obtained.

As a result of the above tests, the following have been found to be preferred:
R is preferably methyl.
"-(CHR$^1$)$_m$-" is preferably -CH$_2$-, -CH$_2$CH$_2$-, or -CH(CH$_3$)CH$_2$-.

Z is preferably:

(a) -OCONHR$^5$ wherein R$^5$ is a C$_{1-4}$ alkyl group;

(b) -N(R$^2$)COR$^3$ wherein R$^2$ is hydrogen or C$_{1-4}$ alkyl, and R$^3$ is a C$_{1-4}$ alkyl group;

(c) -N(R$^2$)SO$_2$R$^3$ wherein R$^2$ is hydrogen or C$_{1-4}$ alkyl, and R$^3$ is C$_{1-4}$ alkyl, phenyl or benzyl; or (d) -N(R$^2$)CONHR$^5$ wherein R$^2$ is hydrogen or C$_{1-4}$ alkyl, and R$^5$ is a C$_{1-4}$ alkyl group.

The most preferred individual compounds are those of the formula (I) in which R is CH$_3$ and Y is either:

-CH$_2$CH$_2$OCONHC$_2$H$_5$,
-CH$_2$CH$_2$NHSO$_2$CH$_3$,
-CH$_2$CH$_2$N(CH$_3$)SO$_2$CH$_3$,
-CH$_2$N(CH$_3$)CONH(CH$_2$)$_2$CH$_3$,
-CH$_2$CH$_2$N(CH[CH$_3$]$_2$)SO$_2$CH$_3$,
-CH(CH$_3$)CH$_2$N(CH$_3$)SO$_2$CH$_3$,
-CH(CH$_3$)CH$_2$N(CH$_3$)COCH$_3$,
-CH$_2$N(CH$_3$)CONH(CH$_2$)$_3$CH$_3$,
or -CH(CH$_3$)CH$_2$N(CH$_3$)SO$_2$C$_2$H$_5$.

The invention also includes the pharmaceutically acceptable bioprecursors of the compounds of the formula (I).

DETAILED DESCRIPTION OF THE INVENTION

The term "pharmaceutically acceptable bioprecursor" requires some explanation. It is, of course, common practice in pharmaceutical chemistry to overcome some undesirable physical or chemical property of a drug by converting the drug into a chemical derivative which does not suffer from that undesirable property, but which, upon administration to an animal or human being, is converted back to the parent drug. For example, if the drug is not well absorbed when given to the animal or patient, by the oral route, it is possible to convert the drug into a chemical derivative which is well absorbed and which the serum or tissues is reconverted to the parent drug. Again, if a drug is unstable in solution, it is possible to prepare a chemical derivative of the drug which is stable and can be administered in solution, but which is reconverted in the body to give the parent drug. The pharmaceutical chemist is well aware of the possibility of overcoming intrinsic deficiencies in a drug by chemical modifications which are only temporary and are reversible upon administration to the animal or patient.

For the purpose of this specification the term "pharmaceutically acceptable bioprecursor" of a compound of the formula (I) means a compound having a structural formula different from the compounds of the formula (I) but which nonetheless, upon administration to an animal or human being, is converted in the patient's body to a compound of the formula (I).

The compounds of the invention can be administered alone but will generally be administered in admixture with a pharmaceutical carrier selected with regard to the intended route of administration and standard pharmaceutical practice. For example they can be administered orally in the form of tablets containing such excipients as starch or lactose, or in capsules either alone or in admixture with excipients, or in the form of elixirs or suspensions containing flavoring or coloring agents. They can be injected parenterally, for example, intravenously, intramuscularly or subcutaneously. For parenteral administration, they are best used in the form of a sterile aqueous solution which can contain other solutes, for example, enough salts or glucose to make the solution isotonic.

For administration to man in the curative or prophylactic treatment of cardiac conditions such as congestive heart failure, oral dosages of the most active compounds of the invention range from 20 mg. to 1 g. daily, taken in 2 to 4 divided doses per day, for an average adult patient (70 kg.). Dosages for intravenous administration range from 1 to 300 mg. per single dose as required, for example in the treatment of acute heart failure. Thus, for a typical adult patient, individual tablets or capsules can conveniently contain from 5 to 250 mg. of active compound, in a suitable pharmaceutically acceptable vehicle or carrier.

Thus, the present invention provides a pharmaceutical composition comprising a compound of the formula (I) as defined above or pharmaceutically acceptable acid addition salt thereof together with a pharmaceutically acceptable diluent or carrier.

The invention also provides a method of stimulating the heart of an animal, including a human being, which comprises administering to the animal a compound of the formula (I) or salt thereof as defined above, or a pharmaceutical composition as defined above, in an amount sufficient to stimulate the heart of the animal.

The compounds of the invention can be prepared by a number of routes:

Route A

Compounds of the formula (I) can be prepared by reacting an appropriately substituted quinazoline of the formula:

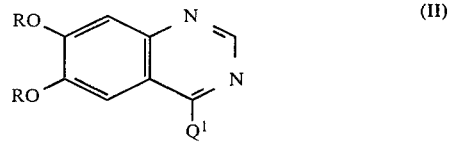

wherein Q$^1$ represents a facile leaving group such as chloro-, bromo-, iodo-, lower alkoxy or (lower alkyl)-thio, with an amine of the formula:

with resultant elimination of HQ$^1$. Q$^1$ is preferably chloro or bromo. The reaction is preferably carried out in an inert organic solvent such as ethanol with heating, e.g. under reflux, in a temperature range of 75° C. to 150° C. for up to about 4 hours. When Q$^1$ is chloro-, bromo- or iodo-, the presence of a base such as triethylamine or of excess reagent of the formula (III) is advantageous.

The product can be isolated and purified by conventional methods.

The compounds of the formula (III) are either known compounds or can be prepared by procedures analogous to the prior art, e.g. by the hydrogenation of the corresponding pyridine derivatives which can themselves be prepared by conventional methods.

Route B

Compounds of the formula (I) in which Z is -N(R$^2$)-CONHR$^5$ can be prepared by the reaction of a quinazoline of the formula:

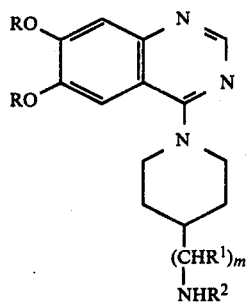

(IV)

with an isocyanate R$^5$NCO, R$^5$ being other than hydrogen, or, to prepare compounds in which R$^5$ is H, sodium or potassium cyanate in the presence of acid. The acid can be supplied by using an acid-addition salt of the compound of the formula (IV) as the starting material. The reaction is typically carried out by stirring the reactants together in an inert organic solvent, e.g. chloroform, at room temperature for up to about 72 hours. The product can be isolated and purified by conventional procedures.

The starting materials of the formula (IV) can be prepared by conventional procedures.

Route C

Compounds of the formula (I) wherein Z is -OCONHR$^5$ can be prepared by reacting a quinazoline of the formula:

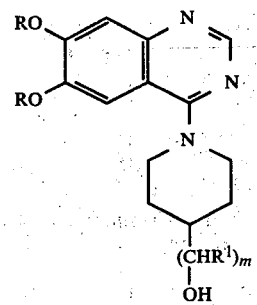

(V)

with an isocyanate R$^5$NCO, R$^5$ being other than hydrogen, or, to prepare compounds in which R$^5$ is hydrogen, sodium or potassium cyanate in the presence of acid. The reaction is typically carried out by stirring the reactants together in an inert organic solvent, e.g., chloroform, at room temperature for up to 24 hours, although some heating may be necessary.

The starting materials of the formula (V) can be prepared by conventional procedures.

The final product can be isolated and purified by conventional methods.

Acid addition salts of the compounds of formula (I) can be prepared from the crude or pure free base product by the conventional technique of reacting the free base with the acid in an inert solvent, e.g. by mixing alcoholic solutions of each and collecting the resulting precipitate by filtration. The product can then be recrystallized to purity.

The quinazoline starting materials used in the preceding routes can be prepared by procedures analogous to those of the prior art. Similarly the piperidine and other starting materials used are either known compounds or can be prepared by conventional methods.

The following Examples illustrate the invention:

EXAMPLE 1

Preparation of 6,7-Dimethoxy-4-[4-(2-methanesulphonamidoethyl) piperidino]quinazoline

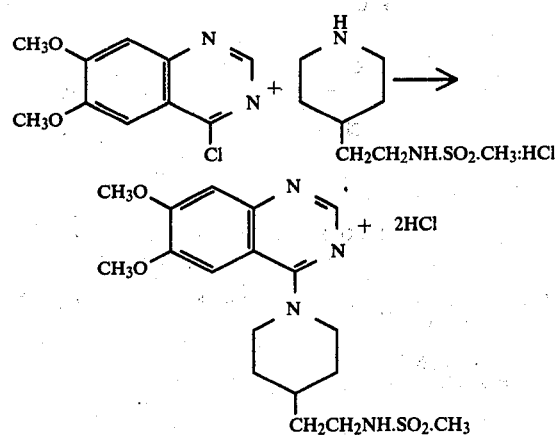

4-Chloro-6,7-dimethoxy quinazoline (1.1 g.), 4-(2-methanesulphonamidoethyl)piperidine hydrochloride (1.5 g.) and triethylamine (1.5 ml.) in ethanol (30 ml.) were heated together under reflux for 1.5 hours. The solution was then cooled to room temperature, concentrated in vacuo, suspended in water (70 ml.) and basified to pH 10 with 10% aqueous sodium carbonate solution. The mixture was extracted with chloroform (2×70 ml.), the extracts combined, dried (MgSO$_4$), and taken to dryness in vacuo. The resultant pale yellow oil was triturated with ether (70 ml.) to give a white solid which was collected by filtration. Crystallization of this solid from ethanol yielded 6,7-dimethoxy-4-[4-(2-methanesulphonamidoethyl)-piperidino]quinazoline (1.7 g.), m.p. 162°–164° C.

Analysis %: Found: C, 54.8; H, 6.6; N, 14.4:
Calculated for C$_{18}$H$_{26}$N$_4$O$_4$S: C, 54.8; H, 6.6; N, 14.2.

The following compounds were prepared similarly to Example 1, starting from 4-chloro-6,7-dimethoxyquinazoline and the appropriate 4-substituted piperidine:

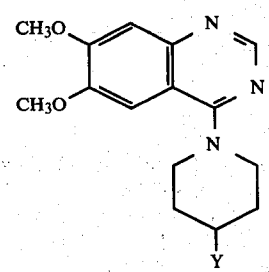

| Example No. | Y | Form Isolated and m.p. (°C.) | Analysis % (Theoretical in Brackets) | | |
|---|---|---|---|---|---|
| | | | C | H | N |
| 2 | —CH₂CH₂NHCONHC₂H₅ | Free base, 198°–201° | 61.7 (62.0) | 7.6 7.5 | 18.2 18.1) |
| 3 | —CH₂NHCOCH₃ | Free base, 177°–181° | 62.4 (62.8) | 6.9 7.0 | 16.2 16.3) |
| 4 | —CH₂CH₂N(CH₃)SO₂CH₃ | Free base, 175° | 55.4 (55.9) | 7.0 6.9 | 13.9 13.7) |
| 5 | —CH₂CH₂N(CH₃)CONHC₂H₅ | Free base, 170°–171° | 62.1 (62.8) | 7.7 7.8 | 17.3 17.4) |
| 6 | —CH₂N(CH₃)CONH(CH₂)₂CH₃ | Free base, 163–165° | 62.6 (62.8) | 7.8 7.8 | 17.2 17.4) |
| 7 | —CH₂CH₂NHSO₂.Phenyl | Free base, 178°—180° | 60.2 (60.5) | 6.1 6.2 | 11.7 12.3) |
| 8 | —CH₂CH₂N(CH[CH₃]₂)SO₂CH₃ | Hydrochloride, 221°–224° | 53.0 (53.3) | 7.1 7.0 | 11.8 11.8) |
| 9 | —CH(CH₃)CH₂N(CH₃)SO₂CH₃ | Hydrochloride monohydrate, 183°–188° | 50.5 (50.4) | 7.0 7.0 | 11.7 11.7) |
| 10 | —CH(CH₃)CH₂N(CH₃)COCH₃ | Free base, 137°–139° | 65.0 (65.3) | 8.0 7.8 | 14.7 14.5) |
| 11 | —CH₂CH₂N(CH₃)CO(CH₂)₂CH₃ | Oxalate, 172°–174° | 57.8 (58.8) | 7.0 7.0 | 11.3 11.4) |
| 12 | —CH₂CH₂N(CH₃)SO₂.benzyl | Hydrochloride monohydrate, 169°–172° | 55.7 (55.7) | 6.3 6.5 | 10.0 10.4) |
| 13 | —CH₂N(CH₃)CONH(CH₂)₃CH₃ | Free base, 154°–157° | 63.8 (63.6) | 7.8 8.0 | 16.7 16.9) |
| 14 | —CH₂CH₂N(CH₃)SO₂(CH₂)₂CH₃ | Free base, 132°–134° | 57.6 (57.8) | 7.5 7.4 | 12.4 12.8) |
| 15 | —CH(CH₃)CH₂N(CH₃)SO₂C₂H₅ | Oxalate, 159°–161° | 52.1 (52.5) | 6.5 6.5 | 10.5 10.6) |

EXAMPLE 16

Preparation of
6,7-dimethoxy-4-[4-(3-n-butylureidomethyl)piperidino]-quinazoline

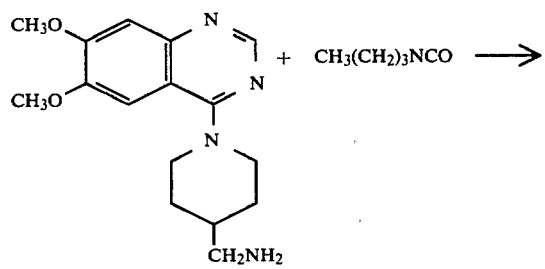

n-Butylisocyanate (1.8 g.) was added to a stirred solution of 6,7-dimethoxy-4-[4-(aminomethyl)piperidino]-quinazoline (5 g.) in dry chloroform (100 ml.). The mixture was then stirred at room temperature for 3 hours, then left standing for 72 hours. An equal volume of 1 N hydrochloric acid was added, the organic phase separated, and the aqueous phase basified to pH 10 with aqueous potassium carbonate solution. The mixture was extracted with chloroform (2×100 ml.), the extracts combined, dried (MgSO₄), and taken to dryness in vacuo. The resultant solid was recrystallized twice from acetonitrile and then once from a mixture of isopropanol and ether to yield 6,7-dimethoxy-4-[4-(3-n-butylureidomethyl) piperidino]quinazoline (3.3 g.), m.p. 141°–143° C.

Analysis %: Found: C, 62.7; H, 7.8; N, 17.7:
Calculated for C₂₁H₃₁N₅O₃: C, 62.8; H, 7.8; N, 17.4

EXAMPLE 17

Preparation of
6,7-Dimethoxy-4-[4-(2-N-ethylcarbamoyloxyethyl)piperidino]quinazoline

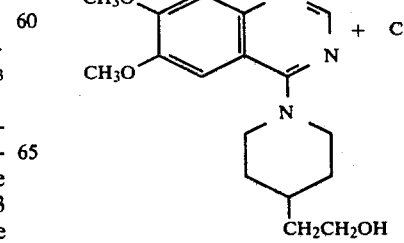

-continued

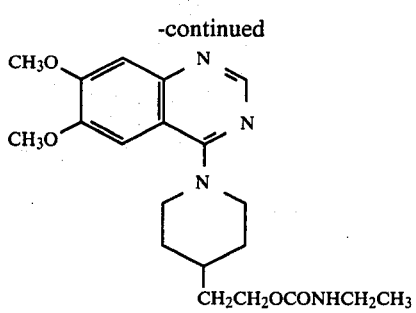

CH2CH2OCONHCH2CH3

6,7-Dimethoxy-4-[4-(2-hydroxyethyl)piperidino]-quinazoline (1.5 g.) and ethyl isocyanate (4 g.) were stirred together in dry chloroform (50 ml.) at room temperature for 18 hours, then heated under reflux for 7 hours. The solution was cooled to room temperature and concentrated in vacuo to give a colorless oil which was dissolved in the minimum volume of chloroform and applied to the top of a chromatography column made up of "Florisil" (Trademark) (100 g.) in chloroform. The column was eluted with chloroform/5% methanol. 50 ml. fractions were collected and monitored by thin layer chromatography. Appropriate fractions were combined and taken to dryness in vacuo to yield pure 6,7-dimethoxy-4-[4-(2-N-ethylcarbamoyloxyethyl)piperidino]-quinazoline (0.8 g.), m.p. 145° C.

Analysis %: Found: C, 61.5; H, 7.5; N, 14.5: Calculated for $C_{20}H_{28}N_4O_4$: C, 61.8; H, 7.3; N, 14.4.

EXAMPLE 18

The procedures of Examples 1–17 are repeated but using the appropriate 4-chloro-6,7-dialkoxyquinazoline as reactant in place of 4-chloro-6,7-dimethoxyquinazoline to give the compounds tabulated below:

| R | Y |
|---|---|
| $C_2H_5$ | $CH_2CH_2OCONHC_2H_5$ |
| i-$C_3H_7$ | $CH_2CH_2OCONHC_2H_5$ |
| n-$C_4H_9$ | $CH_2CH_2NHSO_2CH_3$ |
| n-$C_3H_7$ | $CH_2CH_2N(CH_3)SO_2CH_3$ |
| $C_2H_5$ | $CH_2N(CH_3)CONH(CH_2)_2CH_3$ |
| sec-$C_4H_9$ | $CH_2CH_2N(CH[CH_3]_2)SO_2CH_3$ |
| $C_2H_5$ | $CH(CH_3)CH_2N(CH_3)SO_2CH_3$ |
| n-$C_3H_7$ | $CH(CH_3)CH_2N(CH_3)COCH_3$ |
| $C_2H_5$ | $CH_2N(CH_3)CONH(CH_2)_3CH_3$ |
| n-$C_5H_{11}$ | $CH_2CH_2NHSO_2CH_3$ |
| n-$C_6H_{13}$ | $CH_2CH_2OCONHC_2H_5$ |
| n-$C_3H_7$ | $CH(CH_3)CH_2N(CH_3)SO_2C_2H_5$ |
| n-$C_6H_{13}$ | $CH(CH_3)CH_2N(CH_3)SO_2C_2H_5$ |
| n-$C_5H_{11}$ | $CH_2CH_2N(CH[CH_3])SO_2CH_3$ |

The following preparations, in which all temperatures are in °C., illustrate the production of certain of the starting materials used in the previous examples:

PREPARATION 1

(A) Preparation of 4-(2-methanesulphonamidoethyl)pyridine

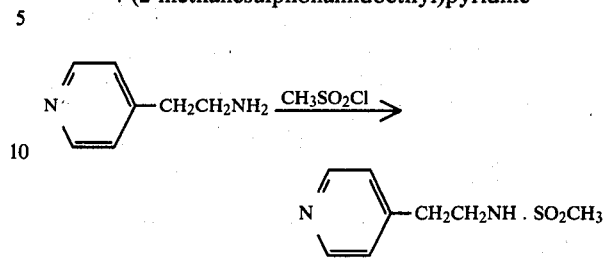

Methanesulphonyl chloride (3.5 g.) was added slowly to 4-(2-aminoethyl)pyridine (3.6 g.) and triethylamine (3.0 g.) in chloroform (40 ml.). The temperature was maintained below 40° C. during the addition, after which the orange solution was left to stand at room temperature overnight. Water (50 ml.) was then added, the chloroform phase was separated, and the aqueous phase extracted with chloroform (100 ml.). The two chloroform solutions were combined, dried ($MgSO_4$) and taken to dryness in vacuo to give a yellow oil which solidified immediately. This solid was crystallized from ethanol to yield white crystals of 4-(2-methanesulphonamido-ethyl)pyridine (1.4 g.).

A small sample was recrystallized from ethanol, m.p. 114°–116° C.

Analysis %: Found: C, 47.9; H, 6.0; N, 14.0: Calculated for $C_8H_{12}N_2O_2S$: C, 48.0; H, 6.0; 25 N, 14.0.

(B) Preparation of 4-(2-methanesulphonamidoethyl)piperidine

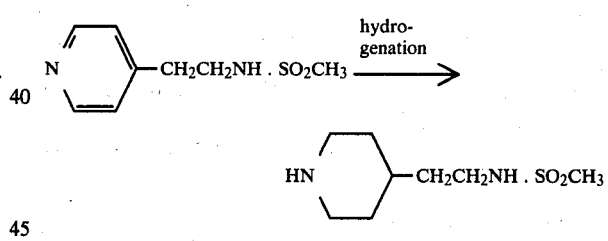

4-(2-Methanesulphonamidoethyl)pyridine (8.4 g.) in ethanol (85 ml.) was acidified to pH 2 with 2 N HCl and hydrogenated at room temperature and a pressure of 50 p.s.i. over a platinum oxide catalyst until hydrogen uptake ceased. The catalyst was then removed by filtration and the filtrate was taken to dryness in vacuo to give a white solid which was dissolved in the minimum volume of hot ethanol, filtered quickly, and left at room temperature overnight. The resultant white crystals were collected by filtration and dried to yield 4-(2-methanesulphonamidoethyl)piperidine:hydrochloride (8.3 g.), m.p. 165°–167° C.

Analysis %: Found: C, 39.6; H, 7.8; N, 11.7: Calculated for $C_8H_{18}N_2O_2S\cdot HCl$: C, 39.6; H, 7.9; N, 11.5.

Also synthesized in a similar fashion to part (A) using the appropriate sulfonyl chloride or acid chloride were:

4-(2-[N-iso-propyl-methanesulphonamido]ethyl)-pyridine oxalate, m.p. 129°–131° C., Found: C, 46.7; H, 6.2; N, 8.0%; $C_{11}H_{18}N_2O_2S\cdot C_2H_2O_4$ requires: C, 47.0; H, 6.1; N, 8.4%

4-(2-[N-Methyl-methanesulphonamido]ethyl)pyridine (crude oil);

4-(2-Benzenesulphonamidoethyl) pyridine, m.p. 109°–110° C., Found: C, 59.5; H, 5.4; N, 10.6%; $C_{13}H_{14}N_2O_2S$ requires: C, 59.5; H, 5.4; N, 10.7% dl-4-(1-[N-Methyl-methanesulphonamido]prop-2-yl)-pyridine oxalate, m.p. 155°–158° C.

4-(2-[N-Methyl-phenylmethanesulphonamido]ethyl)-pyridine, m.p. 109°–110° C.; Found: C, 62.0; H, 6.3; N, 9.7%; $C_{15}H_{18}N_2O_2S$ requires: C, 62.1; H, 6.3; N, 9.7%

4-(2-[N-Methyl-propanesulphonamido]ethyl)pyridine; dl-4-(1-[N-Methyl-ethanesulphonamido]prop-2-yl)-pyridine, and 4-(2-[N-Methyl-butyramido]ethyl)pyridine.

The above were then hydrogenated similarly to Part (B) to give the corresponding piperidines.

PREPARATION 2

(A) 4-(3-n-Butyl-1-methylureidomethyl)pyridine 4-(N-Methylaminomethyl)pyridine (3.6 g.) in dry chloroform (70 ml.) was stirred and cooled in an ice bath while n-butylisocyanate (9.9 g.) was added slowly, dropwise.

The mixture was then allowed to stand at ambient temperature overnight after which methanol (15 ml.) was added and stirring continued for a further 30 minutes. The solvents were removed by evaporation to dryness in vacuo and the residue was redissolved in ethyl acetate (50 ml.). The oxalate salt was precipitated by treating the solution with a slight excess of oxalic acid in ethyl acetate. Recrystallization from isopropanol gave pure 4-(3-n-butyl-1-methylureidomethyl)pyridine sesqui-oxalate (7.2 g.), m.p. 86°–90° C.

Analysis %: Found: C, 50.4; H, 6.6; N, 11.9: $C_{12}H_{19}N_3O.1\frac{1}{2}(C_2H_2O_4)$ requires: C, 50.6; H, 6.2; N, 11.8.

Also synthesized by a similar method were:

4-(2-[3-Ethylureido[ethyl)pyridine (crude base, unpurified),

4-[1-Methyl-3-n-propylureidomethyl)pyridine (crude base, unpurified), 4-(2-[3-Ethyl-1-methylureido]ethyl)pyridine (crude base, unpurified).

(B) The above pyridines were then hydrogenated to the corresponding piperidines similarly to Preparation 1(B)

PREPARATION 3

(A) Preparation of 6,7-Dimethoxy-4-[4-(aminomethyl)-piperidino]quinazoline

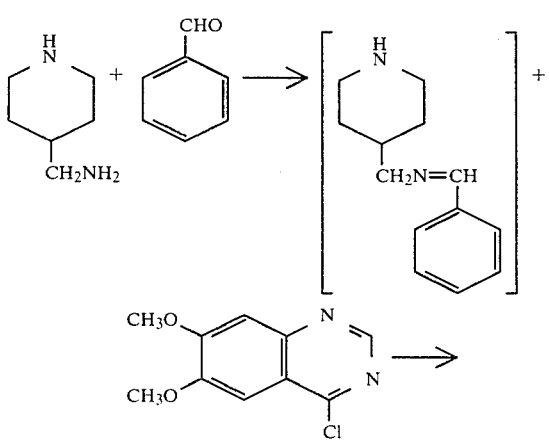

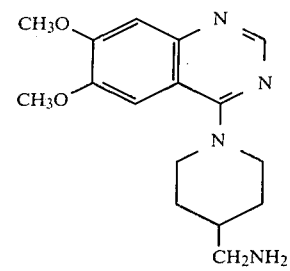

4-(Aminomethyl)piperidine (11.4 g.) and benzaldehyde (10.6 g.) in benzene (200 ml.) were heated under reflux in a flask fitted with a Dean and Stark watertrap. Although liberation of water had virtually ceased after 4 hours, heating was continued for a further 8 hours. The benzene was then removed in vacuo to give an oil.

The above preparation was repeated on the same scale and the two products were combined to give crude 4-(benzylidene-aminomethyl)piperidine (22.5 g.).

Crude 4-(benzylideneaminomethyl)piperidine (20 g.) and 4-chloro-6,7-dimethoxyquinazoline (22.5 g.) in dimethylacetamido (500 ml.) were allowed to stand together at room temperature for 72 hours.

The mixture was then taken to dryness in vacuo to give a solid which was triturated with ether (150 ml.) and filtered. The ether filtrate was taken to dryness in vacuo, the resultant oil was heated at 95° C. for 1½ hours with concentrated HCl (10 ml.), diluted with water (20 ml.) and extracted with chloroform (2×100 ml.). The chloroform extract was washed with water (2×20 ml.) and the aqueous washings were combined with the diluted acid solution remaining from the chloroform extraction and basified to pH 11 with aqueous sodium hydroxide. The basic solution was then extracted with chloroform (2×100 ml.) and the extracts were dried (MgSO4) - Solution A.

The solid collected from trituration with ether was stirred with chloroform and filtered. The chloroform filtrate was treated in the same manner as the previous ether filtrate to give Solution B.

Solutions A and B were combined, taken to dryness in vacuo and crystallized from methylcyclohexane to yield 6,7-dimethoxy-4-[4-(aminomethyl)piperidino]-quinazoline (11 g.), m.p. 144°–146° C.

Analysis %: Found: C, 63.3; H, 7.3; N, 17.8: Calculated for $C_{16}H_{22}N_4O_2$: C, 63.6; H, 7.3; N, 18.5.

PREPARATION 4 dl-4-(1-[N-Methylacetamido]prop-2-yl)pyridine dl-4-(1-Methylaminoprop-2-yl)pyridine (4.5 g.) in acetic acid (15 ml.) was treated cautiously with acetic anhydride (10 ml.) followed by allowing the mixture to stand at ambient temperature overnight. Methanol (20 ml.) was then added to destroy excess acetic anhydride, followed by evaporation in vacuo (at 40° C.) to remove methanol and methyl acetate. The residue was diluted with water and treated portionwise with sodium carbonate (anhydrous) until alkaline (pH 10-12). The oily suspension was extracted with chloroform (3×60 ml.) and the bulked extracts were dried (Na2CO3) and evaporated to dryness in vacuo to give a near-colorless oil (6.8 g.). The oil was distilled to give pure dl-4-(1-[N-methylacetamido]prop-2-yl)pyridine (3 g.), b.p. 138°–140°/0.4 mm Hg. (as a colorless oil).

Analysis %: Found: C, 65.8; H, 8.5; N, 14.2: $C_{11}H_{16}N_2O \cdot \frac{1}{2}H_2O$ requires: C, 65.7; H, 8.4; N, 13.9.

The following compound was synthesized by a similar method:

4-(Acetamidomethyl)pyridine, m.p. 83°–88° C.

The above were then hydrogenated similarly to Example 1(B) to give the corresponding piperidines.

PREPARATION 5

4-(2-isopropylaminoethyl)pyridine 4-Vinylpyridine (21 g.), isopropylamine (24 g.), concentrated hydrochloric acid (40 g.) and water (100 ml.) were mixed together with cooling and then boiled under reflux for 20 hours. The mixture was cooled, basified to pH 12–13 (20% NaOH) and extracted with chloroform (3×200 ml.). The bulked extracts were washed with water (100 ml.), dried ($MgSO_4$) and evaporated in vacuo to give a green oil. The oil was distilled and the fraction boiling at
84°–90° C./1 mm. was collected (16.5 g.) and identified(by NMR spectroscopy) as
4-(2-isopropylaminoethyl)pyridine.

Also synthesized by a similar route were:
4-(2-Aminoethyl)pyridine,
4-(2-Methylaminoethyl)pyridine, and
dl-4-(1-Methylaminoprop-2-yl)pyridine.

What is claimed is:

1. A compound of the formula:

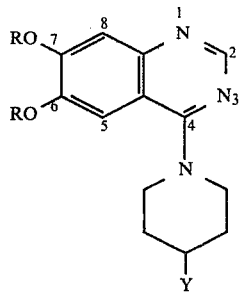

(I)

wherein R is a lower alkyl group; and
Y represents a group of the formula:

$-(CHR^1)_m-Z$ wherein $R^1$ is selected from the group consisting of hydrogen and lower alkyl; m is 1 or 2, with the proviso that when m is 2, each $R^1$ may be the same or different; and Z is selected from the group consisting of $-OCONR^4R^5$;
$-N(R^2)COR^3$;
$-N(R^2)SO_2R^3$; and
$-N(R^2)CONR^4R^5$;

wherein $R^2$ is selected from the group consisting of hydrogen and lower alkyl; $R^3$ is selected from the group consisting of alkyl, benzyl and phenyl; and $R^4$ and $R^5$ are each independently selected from the group consisting of hydrogen and a group as defined for $R^3$ above; and the pharmaceutically acceptable acid addition salts thereof.

2. A compound according to claim 1 wherein R is methyl.

3. A compound according to claim 2 wherein $-(CHR^1)_m-$ is selected from the group consisting of $-CH_2-$, $-CH_2CH_2-$ and $-CH(CH_3)CH_2-$.

4. A compound according to claim 3 wherein Z is $-OCONR^4R^5$.

5. A compound according to claim 3 wherein Z is $-N(R^2)SO_2R^3$.

6. A compound according to claim 3 wherein Z is $-N(R^2)CONR^4R^5$.

7. A compound according to claim 3 wherein Z is $-N(R^2)COR^3$.

8. The compound according to claim 4 wherein $-(CHR^1)_m-Z$ is $-CH_2CH_2OCONHC_2H_5$, said compound being 6,7-dimethoxy-4-[4-(2-N-ethylcarbamoyloxyethyl)piperidino]-quinazoline.

9. The compound according to claim 5 wherein $-(CHR^1)_M-Z$ is $CH_2CH_2NHSO_2CH_3$, said compound being 6,7-dimethoxy-4-[4-(2-methanesulphonamidoethyl)piperidino]-quinazoline.

10. The compound according to claim 5 wherein $-(CHR^1)_m-z$ is $-CH_2CH_2N(CH_3)SO_2CH_3$, said compound being 6,7-dimethoxy-4-[4-(2-N-methylmethanesulphonamido-ethyl)piperidino]quinazoline.

11. The compound according to claim 6 wherein $-CHR^1)_m-Z$ is $-CH_2N(CH_3)CONH(CH_2)_2CH_3$, said compound being 6,7-dimethoxy-4-[4-(1-methyl-3-n-propylureidomethyl)piperidino]quinazoline 12. A compound according to claim 7 wherein Z is $-(CHR^1)_m-Z$ is $-CH(CH_3)CH_2N(CH_3)COCH_3$, said compound being 6,7-dimethoxy-4-[1-methylacetamidoprop-2-yl)piperidino]quinazoline.

13. A pharmaceutical composition comprising a cardiac stimulating amount of a compound according to claim 1, or a pharmaceutically acceptable acid addition salt thereof, together with a pharmaceutically acceptable diluent or carrier.

* * * * *